United States Patent
Sendl-Lang et al.

[11] Patent Number: 5,972,376
[45] Date of Patent: Oct. 26, 1999

[54] TRANSDERMAL SYSTEM OF TACRINE/SELEGILIN-PLASTER

[75] Inventors: Anna Sendl-Lang; Wilfried Fischer, both of Holzkirchen, Germany

[73] Assignee: Hexal, A.G., Munich, Germany

[21] Appl. No.: 09/043,231

[22] PCT Filed: Sep. 12, 1996

[86] PCT No.: PCT/EP96/04010

§ 371 Date: Mar. 12, 1998

§ 102(e) Date: Mar. 12, 1998

[87] PCT Pub. No.: WO97/09969

PCT Pub. Date: Mar. 20, 1997

[30] Foreign Application Priority Data

Sep. 12, 1995 [DE] Germany .......................... 195 33 772

[51] Int. Cl.⁶ ..................................................... A61F 13/00
[52] U.S. Cl. ........................................... 424/449; 424/448
[58] Field of Search ...................................... 424/448, 449

[56] References Cited

U.S. PATENT DOCUMENTS

| | | |
|---|---|---|
| 4,668,232 | 5/1987 | Cordes et al. . |
| 4,812,481 | 3/1989 | Reischig et al. . |
| 4,861,800 | 8/1989 | Buyske . |
| 5,019,395 | 5/1991 | Mahjour et al. . |
| 5,312,817 | 5/1994 | Snorrason . |

FOREIGN PATENT DOCUMENTS 1336071  6/1995  Canada .

*Primary Examiner*—D.Gabrielle Brouillette
*Attorney, Agent, or Firm*—Brooks & Kushman P.C.

[57] ABSTRACT

The invention relates to a plaster for transdermal application with an outer covering or backing layer, a self-adhesive matrix or a reservoir and a removable protective liner or release layer, the matrix or the reservoir containing tacrine and selegiline (optionally in the form of their pharmaceutically compatible salts) as active substance.

25 Claims, No Drawings

TRANSDERMAL SYSTEM OF TACRINE/SELEGILIN-PLASTER

This application is a 371 of PCT/EP96/04010, filed Sep. 12, 1996.

Tetrahydroaminoacridine (tacrine) is used as a centrally active choline esterase inhibitor in the case of Alzheimer's disease. Its choline esterase inhibition lasts for approximately 15 hours, i.e. considerably longer than the half-life of tacrine which is in the region of 1.5 to 3.5 h. The daily recommended dose varies between 30 and 160 mg, the therapeutic blood level being in the range of 5 to 70 ng/ml and the bioavailability in the region of 10 to 30%. In the case of patients who suffer from Alzheimer's disease and are being treated over a prolonged period with several doses of tacrine per day, a clinical improvement in the memory and the functional autonomy can be observed.

Tacrine is used orally in the form of the hydrochloride (Cognex®). Since the oral administration of tacrine must take place in the form of multiple dosages, because of its short elimination half-life, while on the other hand the release of the active substance should remain constant over a long period, a transdermal administration would represent a more effective drug therapy. An additional problem is posed by the strong first pass metabolisation and the greatly varying pharmacokinetics of tacrine which lead to a poor adjustability of the patients, the occurrence of blood plasma peaks and an increase in the secondary effects and the toxicity, particularly to the liver. The hepatotoxic effect of tacrine occurs in the case of approximately half of the patients, an increase in the ALT (alanine aminotransferase) values to as much as 20 times the upper normal limit being observed. By way of a continuous transdermal administration of tacrine, more constant and lower therapeutically effective plasma levels and consequently reduced secondary effects, particularly on the liver, might be obtained, in particular since the high first pass effect and the low bioavailability should no longer occur.

In EP-B-0 332 147, a transdermal system is described with a content of (a) inter alia tetrahydroaminoacridine or a pharmaceutically acceptable salt of this compound as active substance (b) a propylene glycol diester of caprylic acid and capric acid (Migliol) and (c) silicic acid as gelling agent.

Migliol increases the flow of substance through the skin of mice in this transdermal system in comparison with a formulation without Migliol. Optionally, a permeation accelerator in the form of a solvent can be added, e.g. alcohol. However, alcohol irritates the skin, dries it and damages it. The use of ethanol should be assessed critically since it interferes with the natural lipid layer of the skin and dries it and irritates it. In addition, it is stated in EP-B-0 499 662 that the release control of the active substance in the case of plaster according to EP-B-0 332 147 is not an optimal one.

According to EP-B-0 499 662, a two-layer composite laminate is provided as transdermal system which consists of A) a layer I with a component A which consists of solvent and an active substance in a partially cured elastomer and B) a layer II on layer I which comprises a component B which consists of a solvent and an active substance in a macroporous moulded body with a pore size of 10 to 100 μm.

As an example of an active substance, 1,2,3,4-tetrahydro-9-acridinamine (THA=tacrine) is mentioned, inter alia. Alcohols, for example ethanol, are suggested as solvents for components A and B. However, ethanol again dries the skin, irritates and damages it.

Moreover, the spongy transdermal system known from EP-B-O- 499 662 is thick and inflexible and consequently not very practical for application by the patient since the system is exposed as a result of its height, easily involuntarily removable and does not adjust well to body movements.

The transdermal system known from EP-B-O 499 662 is produced by (a) mixing an active substance with a solvent and a curable elastomer component (b) the component A thus obtained is cast to form a partially cured layer I (c) an active substance is dissolved in a solvent (d) the solution obtained is introduced into a macroporous moulded body and component B is obtained which forms layer II (e) layer II is laminated onto layer I and, optionally, the laminate thus obtained is cut into plasters of the desired size.

This production process is difficult to understand, complicated and, moreover, leads to a poorly reproducible blood level, possibly as a result of the partial curing of the elastomer which is difficult to control. If, moreover, an elevated temperature of e.g. 160° C. is used with this highly costly process over several minutes, the active substance may be degraded as a result. Apart from the question of how an aluminium foil should be laminated onto a macroporous sponge, the question remains unanswered as to how the transdermal system can be applied onto the patient since obviously no adhesive element is provided.

According to Auterhoff, Knabe & Höltge, Lehrbuch der Pharmazeutischen Chemie, edition 12, page 484, (R) (–)-N-methyl-N-(1-phenyl-2-propyl)-2-propinylamine (=selegiline=Deprenyl, commercially available as Movergan®), is an anti-Parkinson agent with a dopaminergic effect. EP-A-O 241 809 describes a plaster (column 5, line 15) with a content of selegiline, this plaster being used in combination with a further plaster with a content of amantadine. In addition, a plaster is known as TTS from EP-B-O 404 807 with selegiline as the only active substance, the active substance penetrating from a matrix into the skin. DE-9 523 299 describes a further transdermal system (TTS) with a covering film, a layer with a content of selegiline as active substance, a membrane, a self-adhesive layer and a removable protective layer.

Compared with this state of the art, it is a task of the invention to provide a plaster for transdermal application with which Alzheimer's disease can be fought even more effectively. Another task of the invention consist of increasing the skin permeation of the active substances and of tacrine in particular.

According to a first embodiment of the invention, a transdermal system or plaster with an outer covering or backing layer, a self-adhesive matrix and a removable protective liner or release liner is provided for this purpose, in the case of which the matrix contains tacrine with selegiline (optionally in the form of their pharmaceutically compatible salts) as active substance in addition to a hydrophilic low volatility solvent and/or a lipophilic low volatility solvent.

In view of the efforts made according to EP-B-O 499 662 to provide a plaster with a tacrine content, it could not be expected that satisfactory results could be achieved with a plaster according to the invention. Moreover, the plaster according to the invention can be manufactured cost effectively, reproducibly and without major thermal stress.

The plaster according to the invention is thin, can be tolerated by the skin, is flexible and can be highly satisfactorily applied onto the skin.

The plaster according to the invention differs from a plaster according to EP-B-O 332 147 in that the active substance or substances are not released from a gel using silicic acid as gelling agent but rather from a self-adhesive matrix containing no silicic acid. In the case of the plaster according to the invention it is also possible to deliberately abstain from providing the active substances in two different layers forming a laminate, as in the case of EP-B-O 499 662. Instead, the active substances can be provided in a single layer of the plaster according to the invention, the layer being a self-adhesive matrix.

Since the recommended daily dose for the oral application of tacrine is in the region of 30 to 160 mg and the therapeutic blood level in the region of 5 to 70 ng/ml, it could not be expected that a plaster for transdermal application could be loaded with a comparable amount of active substance and that comparable blood levels could be achieved.

The plaster according to the invention may be characterised by a content of up to 70% by weight (based on the weight of the matrix) of a solvent from the group formed by hydrophilic low volatility solvents, lipophilic low volatility solvents and their mixtures.

In the plaster according to the invention, the two active substances may be present in the matrix in mixture. It is surprising in this respect that the skin permeation can be increased by the presence of selegiline in comparison with a plaster with tacrine as the only active substance.

The matrix in the plaster according to the invention can also contain two matrix layers in sequence, one matrix layer containing one and the other matrix layer the other of the two active substances, the matrix layer adjacent to the outer covering or backing layer being able to contain selegiline or one of its salts or tacrine or one of its salts as active substance. In the case of this embodiment, the two matrix layers may be separated by a membrane which controls the permeation of the active substance from the matrix layer further removed from the skin.

In the plasters according to the invention, the matrix may also contain two or more adjacent zones arranged side by side in the same plane, each containing only one of the two active substances respectively. In this embodiment, the zones may have the form of webs.

The content of tacrine and selegiline (optionally in the form of their salts) can be up to 50% by weight respectively (based on the weight of the matrix) in the plaster according to the invention.

The task on which the invention is based is achieved according to a further embodiment by a plaster for transdermal application with an outer covering or backing layer, a reservoir, an adhesive element for contact between the plaster and the skin and a removable protective liner or release liner, the reservoir containing tacrine and selegiline (optionally in the form of their pharmaceutically compatible salts) as active substances in addition to a solvent from the group formed by hydrophilic low volatility solvents, hydrophobic low volatility solvents, monohydric $C_{2-4}$ alcohols, ethylene glycol and their mixtures.

According to the invention, a membrane, in particular a membrane controlling the permeation of active substance, can be provided.

Membrane and reservoir plasters are part of the state of the art. As an example only, reference should be made to WO-A1-89/09 051, WO-A1-94/23 707, EP-B1-O 404 807 and EP-A1-O 406 488.

For the plaster according to the invention, it is possible to provide a matrix based on polyacrylate, silicone or polyisobutylene. Such matrices are anticipated in the state of the art. As an example only, reference should be made to DE-B-3 933 460 for a polyacrylate matrix, to DE-A-4 339 400 for a silicone matrix and to EP-A-0 186 019 for a polyisobutylene matrix.

In the case of the said embodiment of the plaster according to the invention, the reservoir can be formed by the outer covering or backing layer and the membrane or by a matrix.

The adhesive element can be provided in the form of a layer covering the reservoir (if there is no membrane) or the membrane completely or only on its periphery in an annular manner. According to the invention, the adhesive element can consist of a pressure-sensitive adhesive based on silicone.

The plaster according to the invention can also be characterised by a content of α-tocopherol or α-tocopherol derivative. By means of this addition it is possible to take the critical skin compatibility in the case of the application of low alcohols into account.

It is possible to use, for example, propylene glycol, 1,2-pentane diol, glycerine, hydrophilic Cetiol or Transcutol® as hydrophilic low volatility solvent for a plaster according to the invention. Propylene glycol and glycerine have already been suggested in EP-B-0 499 662, though for the deviating transdermal system discussed above.

Moreover, Copherol®, propylene glycol dicaprylate/dicaprate such as Migliol®, isopropyl myristate or lipophilic Cetiol®, e.g. Cetiol HE, for example, can be used as lipophilic low volatility solvent for the plaster according to the invention. Isopropyl myristate has already been suggested in EP-B-0 332 147 and Migliol® in EP-B-0 332 147 and EP-B-0 499 662, though for the deviating transdermal systems discussed above.

In the case of the plaster according to the invention it is particularly surprising that a combination of hydrophilic low volatility solvents with lipophilic low volatility solvents leads to a substantially higher rate of skin permeation than with each solvent alone.

The plaster according to the invention may also contain a viscosity-enhancing agent such highly dispersed silicon dioxide or hydroxypropylcellulose.

Below, the invention will be explained in further details by examples.

EXAMPLE 1

Single Layer TTS with Tacrine/Selegiline tacrine and selegiline base are dissolved in ethanol. The solution obtained is added to a solution of acrylate adhesive (e.g. Duro-Tak® such as Duro-Tak® 326-1753; National Starch & Chemicals) in ethyl acetate and n-hexane and, optionally, it can be mixed with further auxiliary agents. Subsequently, the solution is applied by means of a doctor blade onto a siliconised polyester film as peel-off film (e.g. Hostaphan®, Hoechst) with a wet layer thickness of 450 µm and dried for 1 hour at 50° C. The dried layer is laminated with a polyester film (or any other suitable covering film). Using a punch, TTS with a surface area of 10, 20, 30 and 40 $cm^2$ are punched from the laminate.

EXAMPLE 2

Two-Layer TTS without a Membrane Controlling the Release of Active Substance Layer A; tacrine base is dissolved in ethanol (optionally together with auxiliary agents). The solution obtained is added to a solution of acrylate adhesive (e.g. Duro-Tak®, such as Duro-Tak® 326-1753; National Starch & Chemicals) in ethyl acetate and n-hexane and mixed homogeneously (optionally with other auxiliary agents). The solution is applied by means of a doctor blade onto a siliconised polyester film (e.g. Gelroflex®, Rexam Release) as peel off film with a wet layer thickness of 450 µm and dried for 1 hour at 50° C.

Layer B; this layer is prepared in an analogous manner to layer A with a single exception, namely that the tacrine base is replaced by the selegiline base.

Subsequently, the dried layer A is laminated onto the second layer B. The peel-off film of the selegiline layer B is peeled off from the two-layer TTS obtained in this way, subsequent to which a thin polyester film (e.g. Hostaphan®; Hoechst) is applied as outer covering layer (backing film) as a replacement for the peeled off film.

EXAMPLE 3

Two-Layer TTS with a Membrane Controlling the Release of Active Substance

In the same way as in example 2, two layers A and B are prepared; however, a membrane controlling the permeation of active substance is provided between these two layers (e.g. Cotran® from 3M; or 1154P). This two-layer TTS is again formed in such a way that it can be bonded onto the skin with the layer containing tacrine.

EXAMPLE 4

Dual Web TTS

Tacrine base on the one hand and selegiline base on the other hand are dissolved according to example 2 and mixed with the acrylate adhesive. Subsequently, two separate webs are laminated side by side onto a peel off film in such a way that one layer contains tacrine and the other layer selegiline. After drying of the dual web layer and laminating an outer covering or backing layer on to it, TTS are punched which contain one web of tacrine and selegiline respectively. Obviously, the proportions of the two active substances can be variably adjusted.

EXAMPLE 5

A pressure-sensitive adhesive based on silicone (trimethylated silicon dioxide treated with polydimethyl siloxane with terminal trimethyl siloxy groups; layer thickness in the dry state (LT) approximately 35 to 45 µm; substance weight (SW) approximately 50 to 60 g/m$^2$) was used for the i- adhesive layer. An outer covering or backing layer of PET (thickness approximately 75 µm, SW approximately 100 g/m$^2$) was coated with the silicone adhesive using a coating device. On to the coated outer covering or backing layer, a microporous polypropylene membrane (heat sealable; thickness approximately 50 µm, SW approximately 120 g/m$^2$) was laminated in such a way that a laminate consisting of the covering layer, adhesive and membrane was produced. Subsequently, the laminate was welded by means of a sealing machine (with welding ring) to a carrier film of polyester (aluminium-metalised) with a polyolefin sealant layer (heat sealable; thickness approximately 70 µm) in such a way that a gap remained for introducing a solution of active substance. The fillable transdermal therapeutic system (empty TTS) was filled e.g. with a Hamilton syringe or with a hose pump with a hollow needle with the following solution of active substance:

Composition of the solution of active substance per TTS:

|  | mg/TTS |
| --- | --- |
| Tacrine base | 40.0 |
| Selegiline base | 20.0 |
| Propylene glycol | 160.0 |
| α-Tocopherol | 80.0 |
| Total | 300.0 mg |

Quantity introduced into the reservoir: 300.0 mg

After filling, the gap used for filling was sealed. Filled transdermal therapeutic systems were punched out by means of a punch.

We claim:

1. A plaster for transdermal application said plaster comprising an outer backing layer, a self-adhesive matrix, and a removable release layer, said matrix further comprising:

A) a first active substance comprising tacrine or a pharmaceutically compatible salt thereof, and a second active substance comprising selegiline or a pharmaceutically compatible salt thereof; and B) a low volatility solvent selected from the group consisting of hydrophilic solvents, lipophilic solvents, and mixtures thereof.

2. A plaster according to claim 1 wherein said low volatility solvent comprises up to 70 percent by weight of said matrix.

3. A plaster according to claim 1 wherein both of said active substances are present in the matrix in admixture.

4. A plaster according to claim 1 wherein said matrix contains two matrix layers in sequence, one matrix layer containing said first active substance, and a second matrix layer containing said second active substance.

5. A plaster according to claim 4 wherein a matrix layer adjacent to the outer backing layer contains said first active substance or said second active substance.

6. A plaster according to claim 4 wherein said two matrix layers are separated by a membrane controlling active substance permeation.

7. A plaster according to claim 1 wherein said matrix comprises two or more adjacent zones arranged side by side in the same plane, each of said zones containing only one of said first and second active substances.

8. A plaster according to claim 7 where said zones are in the form of webs.

9. A plaster according to claim 1 wherein said first active substance and said second active substance together comprise up to 50 percent by weight based on the weight of the matrix.

10. A plaster for transdermal application of tacrine and selegiline comprising an outer covering or backing layer, a reservoir, an adhesive element for contact between said plaster and the skin of a patient, and a removable protective liner or release liner, said reservoir comprising:

A) a first active substance comprising tacrine or a pharmaceutically compatible salt thereof and a second active substance comprising selegiline or a pharmaceutically compatible salt thereof; and B) a low volatility solvent selected from hydrophilic solvents, hydrophobic solvents, and mixtures thereof, and C) optionally, monohydric $C_{2-4}$ alcohols, ethylene glycol, and mixtures thereof.

11. A plaster according to claim 10 further comprising a membrane which controls active substance permeation into the skin.

12. A plaster according to claim 11 wherein said reservoir is formed by said outer covering or backing layer and said membrane.

13. A plaster according to claim 10 wherein said matrix comprises a polyacrylate polymer, a silicone polymer, or a polyisobutylene polymer.

14. A plaster according to claim 1 wherein said matrix comprises a polyacrylate polymer, a silicone polymer, or a polyisobutylene polymer.

15. A plaster according to claim 10 further comprising an adhesive element in the form of a layer completely covering said reservoir.

16. A plaster according to claim 10 further comprising an adhesive element covering the periphery of said membrane in an annular manner.

17. A plaster according to claim 10 further comprising an adhesive element comprising a pressure sensitive silicone adhesive.

18. A plaster according to claim 1 further comprising α-tocopherol or derivative thereof.

19. A plaster according to claim 10 further comprising α-tocopherol or derivative thereof.

20. A plaster according to claim 1 wherein said hydrophilic low volatility solvent comprises propylene glycol, 1,2-pentane diol, glycerin, 2-(2-ethoxyethoxy)ethanol, and mixtures thereof.

21. A plaster according to claim 10 wherein said hydrophilic low volatility solvent comprises propylene glycol, 1,2-pentane diol, glycerin, 2-(2-ethoxyethoxy)ethanol, and mixtures thereof.

22. A plaster according to claim 1 wherein said lipophilic low volatility solvent is selected from the group consisting of propylene glycol dicaprylate/dicaprate, i-propyl myristate, and mixtures thereof.

23. A plaster according to claim 10 wherein said lipophilic low volatility solvent is selected from the group consisting of propylene glycol dicaprylate/dicaprate, i-propyl myristate, and mixtures thereof.

24. The plaster of claim 1, wherein said low volatility hydrophilic solvent is selected from the group consisting of propylene glycol, 1,2-pentane diol, glycerine, 2-(2-ethoxyethoxy)ethanol, and mixtures thereof, and wherein said liophilic low volatility solvent is selected from the group consisting of propylene glycol dicaprylate/dicaprate, i-propyl myristate, and mixtures thereof.

25. The plaster of claim 10, wherein said low volatility hydrophilic solvent is selected from the group consisting of propylene glycol, 1,2-pentane diol, glycerine, 2-(2-ethoxyethoxyl)ethanol and mixtures thereof, and wherein said liophilic low volatility solvent is selected from the group consisting of propylene glycol dicaprylate/dicaprate, i-propyl myristate, and mixtures thereof.

* * * * *